United States Patent [19]

Machiele

[11] 3,952,009
[45] Apr. 20, 1976

[54] PREPARATION OF AZOMETHINES BY REACTING A 4,4-DIHALO-5-PYRAZOLONE WITH AROMATIC PRIMARY AMINES

[75] Inventor: Delwyn Earl Machiele, Rochester, N.Y.

[73] Assignee: Eastman Kodak Company, Rochester, N.Y.

[22] Filed: Dec. 10, 1971

[21] Appl. No.: 206,924

[52] U.S. Cl. .................. 260/310 A; 96/66 HD; 260/310 R; 260/163
[51] Int. Cl. .............. C07d 49/16; C09b 29/38
[58] Field of Search .............. 260/310 R, 310 A

[56] References Cited
OTHER PUBLICATIONS

Curtin et al, J. Am. Chem. Soc., Vol. 83, pp. 3474 to 3481 (1961).

Houben–Weyl, "Methoden Der Organischen Chemie", Vol. X/2, pp. 414 to 417 (1967).

Theilheimer, "Synthetic Methods of Organic Chemistry," Vol. 21, p. 219, paragraph No. 455 (1967).

Zagorevskii et al., Chemical Abstracts, Vol. 61, p. 8264, (1964).

Primary Examiner—Floyd D. Higel
Attorney, Agent, or Firm—G. E. Battist

[57] ABSTRACT

4,4-Dihalo-5-pyrazolones react with unoxidized aromatic primary aromatic amines or alkyl or hydrazines to give azomethine dyes, azo dyes or hydrazones which are useful in photographic systems.

13 Claims, No Drawings

PREPARATION OF AZOMETHINES BY REACTING A 4,4-DIHALO-5-PYRAZOLONE WITH AROMATIC PRIMARY AMINES

This invention relates to new compounds and processes for preparing those compounds. In one aspect, this invention relates to a process of reacting 4,4-dihalo-5-pyrazolones with unoxidized primary aromatic amines. In another aspect, this invention relates to the process of reacting 4,4-dihalo-5-pyrazolones with hydrazines such as phenyl hydrazines whereby azo dyes and hydrazones can be prepared.

It is known in the art to react oxidized color developing agents with color couplers to form indophenols, indoanilines and the like, for example, as disclosed in Fischer, U.S. Pat. No. 1,102,028; Schinzel, U.S. Pat. No. 2,249,541; Mees and James, *The Theory of the Photographic Process*, Third Edition, Chapter 17, 1966; and the like. It is also known that the rates of coupling with oxidized color developers can change with the substituents on the active methylene coupler as disclosed in the last reference above. However, the indophenols, indoanilines, etc., formed in the prior art were often accompanied by a large number of by-products due to the high reactivity of the oxidized color developer, which often gave unwanted products which were difficult to eliminate in purification and also generally gave low product yield. Therefore, improved methods of forming dyes are desired.

I have now found that dye compounds can be readily and efficiently produced by reacting a 4,4-dihalo-5-pyrazolone under basic conditions with an unoxidized primary aromatic amine or a hydrazine. The procedure is very effective in producing azomethine dyes, indoaniline dyes, indophenol dyes, azo dyes, etc., provided that the compound has a 5-pyrazolone moiety and the condensation product of a primary amine.

In one preferred embodiment, this invention relates to the reaction of a 4,4-dihalo-5-pyrazolone with an aminophenol which is preferably an unoxidized aminophenol to produce an indophenol.

In another embodiment, this invention relates to the reaction of a 4,4-dihalo-5-pyrazolone with an unoxidized phenylenediamine to produce an indoaniline.

In still another embodiment, this invention relates to the reaction of a 4,4-dihalo-5-pyrazolone with an alkyl or aryl hydrazine and preferably a phenyl hydrazine to produce an azo dye.

In one preferred embodiment, the reaction is carried out in a polar solvent system with an acid acceptor (i.e., such as a weak base), and in highly preferred systems the polar solvent is dimethylformamide.

Generally, the process of this invention relates to the reaction of a 4,4-dihalo-5-pyrazolone at the coupling position with a compound containing a primary amine and preferably a primary aromatic amine. In the art, 5-pyrazolone couplers are well-known as those compounds having the following nucleus and which couple at the 4-position:

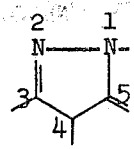

Typical 5-pyrazolone couplers which can be brominated and reacted by the process of this invention include 1-phenyl-3-methyl-5-pyrazolone, 1-phenyl-3-(benzoylamino)-5-pyrazolone, 3-p-nitroanilino-5-pyrazolone, 1-phenyl-3-p-sulfamylphenylamino-5-pyrazolone, 1-phenyl-3-[3-{2-(2,4-di-tert-amylphenoxy)-5-(2-sulfobenzamido)benzamido}benzamido]-5-pyrazolone, 1-[4'-(p-tert-butylphenoxy)phenyl]-3-[α-(p-tert-butylphenoxy)propionamido]-5-pyrazolone, 1-(2,4,6-trichlorophenyl)-3-pentadecyl-5-pyrazolone, and 1-phenyl-3-(p-sec-amylphenyl)-5-pyrazolone. Other useful pyrazolone couplers are disclosed in "Azomethine Dyes. I. Color and Constitution of Pyrazolone Azomethine Dyes", *Journal of the American Chemical Society*, 73, pp. 919–926 (1951), "Purpurkuppler", *Agfa Mitteilungen*, Band II, pp. 126–156, and U.S. Pat Nos. 2,600,788 by Loria et al issued June 17, 1952, 2,369,489 by Porter et al issued Feb. 13, 1945, 2,343,703 by Porter et al issued Mar. 7, 1944, 2,311,082 by Porter et al issued Feb. 16, 1943, 3,152,896 by Tuite issued Oct. 13, 1964, 3,127,269 issued Mar. 31, 1964, 3,519,429 by Lestina issued July 7, 1970, 3,062,653 by Weissberger et al issued Nov. 6, 1962, and 2,908,573 by Bush et al issued Oct. 13, 1959.

The 5-pyrazolone couplers can be halogenated by any halogenating agent known in the art for this purpose. The halogen atoms on the 5-pyrazolone can be chlorine, bromine, iodine or fluorine, and preferably are bromine atoms.

The primary amine compound which can be reacted with the 4,4-dihalo-5-pyrazolone can generally be any organic compound having a primary amine group. However, in making useful dyes, the preferred primary amines are aromatic primary amines or hydrazine compounds having a primary amine (i.e., $NH_2$ group). In one preferred embodiment, the primary aromatic amines are phenylenediamines or aminophenols such as those represented by the formula $H_2N$-Ar-X wherein Ar is an arylene group containing from about 6 to 20 carbon atoms including substituted arylene, unsubstituted arylene, fused-ring arylene and the like, and preferably is a phenylene group which is preferably substituted with halogen atoms or groups containing halogen atoms; and X is an hydroxyl group or an alkyl amine including substituted alkylamines, dialkylamines and the like.

The hydrazine compounds which are useful in forming azo dyes generally have the formula:

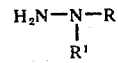

wherein R is an alkyl group, an aryl group and the like and is preferably a phenyl group; and $R^1$ is a hydrogen atom or a lower alkyl group having from 1 to 4 carbon atoms.

The reaction is generally carried out in a polar solvent in a basic medium and is preferably carried out in the presence of an acid acceptor. The polar solvent is generally any one of the organic polar solvents such as dimethylformamide and the like.

The acid acceptor can be any compound useful for the purpose and can include sodium hydroxide, triethylamine, dimethylaniline, sodium carbonate, sodium acetate and the like.

The invention can be further illustrated by the following examples of preferred embodiments thereof.

EXAMPLE 1

Exemplary preparation of 4,4-dibromo-1-phenyl-3-anilino-5-pyrazolone

To a stirred suspension of 12.6 g. (0.05 mol) of 1-phenyl-3-anilino-5-pyrazolone in 100 ml. glacial acetic acid and 10 ml. of water at room temperature are added 18.4 g. (0.12 mol) of $Br_2$ in 40 ml. of glacial acetic acid in several portions. A few minutes after the unsubstituted pyrazolone dissolves, a yellow precipitate is obtained. After 20 minutes of stirring, the precipitate is recovered, washed with water and dried in a vacuum desiccator; m.p. 190°C. with decomposition.

EXAMPLE 2

Hydrazone dye

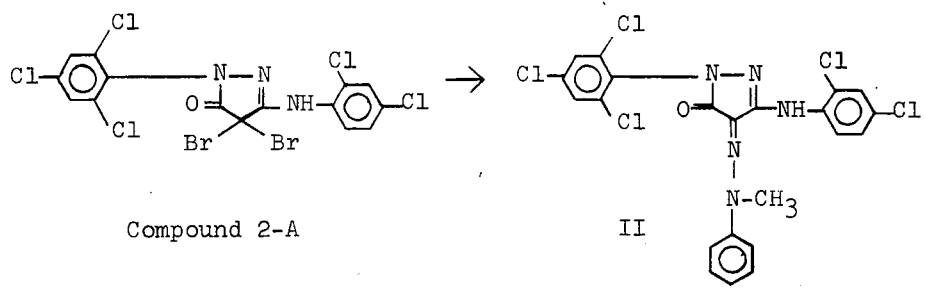

Compound 2-A    II

To a solution of 5.81 g. (0.01 mol) of Compound 2-A in 300 ml. boiling ethanol are added 3.7 g. (0.03 mol) of 1-methyl-1-phenylhydrazine dissolved in 25 ml. of ethanol. After the mixture is heated for 3–5 minutes on a steambath, a precipitate is formed on cooling. This solid is recovered and recrystallized from ethanol; m.p. 226°–228° C. Analysis for $C_{22}H_{14}Cl_5N_5O$: C, 48.8; H, 2.6; Cl, 32.7; N, 12.9.

Found: C, 47.9; H, 2.6; Cl, 32.6; N, 13.0.

EXAMPLE 3

Azo dye

To 1.3 g. (0.002 mol) of the 4,4-dibromo-5-pyrazolone (Compound 2-A) in hot ethanol is added 0.33 g. (0.003 mol) of phenylhydrazine. After heating on a steam pot for 10 minutes, the mixture is cooled and the precipitate which has formed is filtered; m.p. 240°–242° C. This Compound III is identical with a product prepared from the parent pyrazolone by diazonium coupling and is believed to have the formula:

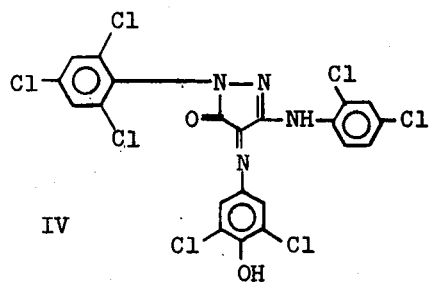

III

EXAMPLE 4

Indophenol dye

To a warm ethanol solution containing 5.8 g. (0.01 mol) of the dibromopyrazolone (Compound 2-A) are added 2.4 g. (0.011 mol) of 4-amino-2,6-dichlorophenol hydrochloride. After this has dissolved, 3.3 g. of triethylamine are added. The solution, which quickly becomes magenta, is stirred for 15 minutes and cooled in an ice-acetone bath. The solid recovered is the dye IV with traces of impurity; m.p. 215°–217° C. (dec.).

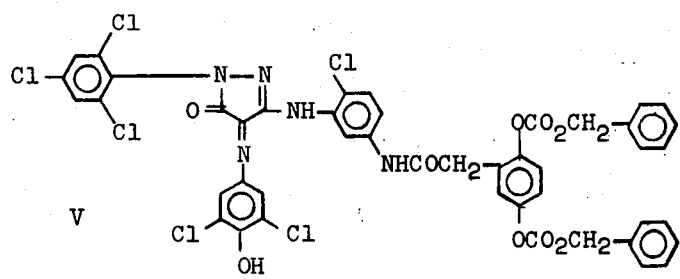

IV

EXAMPLE 5

Indophenol dye

A coupler containing a masked developer moiety is reacted according to the procedure of Example 4 to provide the following indophenol:

V

EXAMPLE 6

Azomethine dye

To a hot solution of 5.8 g. (0.01 mol) of the dibromopyrazolone in ethanol (Compound 2-A) are added 2.1 g. (0.0105 mol) of 4-amino-N,N-diethylaniline hydrochloride. Excess (7–8 ml.) triethylamine is added, forming a magenta dye. The solution is cooled and the precipitate recovered after washing with cold ethanol. The dye shows only one component which is believed to have the formula:

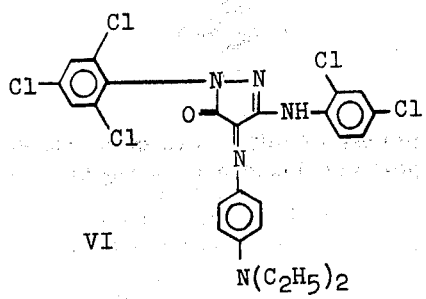

m.p., 212–214° C.

Calculated for $C_{25}H_{20}Cl_5N_5O$: C, 51.4; H, 3.46; Cl, 30.38; N, 12.0.
Found: C, 51.5; H, 3.6; Cl, 29.7; N, 11.9.

EXAMPLE 7

Azomethine dye

Dye VII is prepared from the 4,4-dibromopyrazolone coupler obtained by dibromination of Compound F of Beavers, U.S. Pat. No. 2,983,608. The procedure with the dibromo compound is the same as that given in Example 6 above.

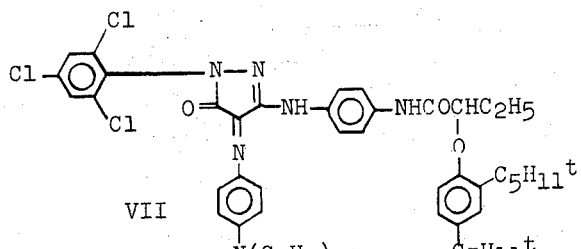

m.p., 142–143° C.

Example 8

The following dibromopyrazolone is reacted with an aminophenol:

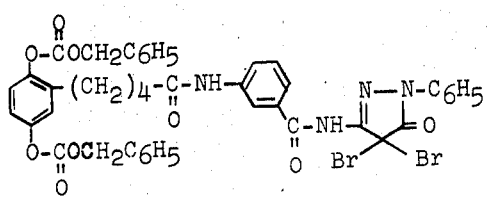

Compound 8-A

A solution of 2,6-dichloro-4-aminophenol (18.2 g., 0.10 mole) in dry dimethylformamide (170 ml.) is added to a stirred solution of Compound 8-A (82.7 g., 0.09 mole) in dry dimethylformamide (800 ml.), followed by immediate addition of triethylamine (33 ml.). After 45 minutes, stirring is halted and the magenta-colored mixture is drowned in ice water. The gummy dye is collected and triturated with an acetone-ethyl acetate-water mixture. An azomethine dye (47.5 g., 55% estimated wt. yield, m.p. 220°–225° C.) is obtained as maroon solids, estimated to be 91.5% pure. Second (2.2 g.) and third (21.5 g.) crops of the dye (additional 27% yield) are obtained by concentration of the mother liquors and dilution with hexane.

Calculated: C, 62.3; H, 3.72; Cl, 8.0; N, 7.5.
Found: C, 62.7; H, 3.5; Cl, 7.7; N, 7.4.

The product is an indophenol, i.e., the condensation product of Compound 8-A and the aminophenol.

The reactions of this invention are run under conditions where the primary amine-containing compound will react with the 4,4-dihalo-5-pyrazolone at the coupling position to produce a dye having an azomethine linkage (>C=N—) or an azo dye having the typical azo linkage (—N=N—). The primary amine is generally present in the reaction vessel in substantially equimolar amounts with the pyrazolone compound; however, in some instances it is desirable to add an excess of the primary amine to the reaction mixture, for example, in some embodiments it is desirable to add up to a 20% molar excess of the primary amine.

The reactions can be run over a wide temperature range which can vary from the freezing point of the mixture to the steam bath temperature and even higher. However, temperatures of 10° C. to 100° C. are generally preferred. The time of the reaction will, of course, be dependent on other reaction conditions, but in one preferred embodiment, reaction times of less than an hour are desired when the temperature is controlled at 20° C. to 120° C.

The instant reaction is preferably and conveniently effected under atmospheric pressure, although higher pressures or even subatmospheric pressures can be utilized.

The dyes produced by the process of this invention can be used for most dyeing applications where dyes of this type are suitable. The dyes having developing agent moieties prepared by this process are especially useful in the systems as disclosed in Lestina and Bush, U.S. Ser. No. 206,836, entitled "Oxichromic Compounds", filed on even date herewith, and now abandoned and the dyes also can be stabilized and used in products as set forth in Stern and Machiele, U.S. Ser. No. 206,926, entitled "Stabilized Oxichromic Compounds", filed on even date herewith.

Although the invention has been described in considerable detail with particular reference to certain preferred embodiments thereof, variations and modifications can be effected within the spirit and scope of the invention.

I claim:

1. A process comprising reacting a 4,4-dihalo-5-pyrazolone compound with an aromatic compound having the formula $H_2N$-Ar-X, wherein Ar is an arylene group containing from 6 to 20 carbon atoms and X is an hydroxy group or an alkylamino group, wherein an azomethine linkage is formed where said pyrazolone reacts with said aromatic compound.

2. A process according to claim 1 wherein said reaction is carried out in a liquid medium in the presence of a polar solvent.

3. A process according to claim 2 wherein said polar solvent is dimethylformamide.

4. A process according to claim 1 wherein said arylene group is a phenylene group.

5. A process according to claim 1 wherein said reaction is carried out in a liquid medium in the presence of a polar solvent and triethylamine.

6. A process according to claim 2 wherein said reaction is carried out in a basic liquid medium.

7. A process of forming a photographic image dye compound where a photographic 4,4-dihalo-5-pyrazolone color coupler is reacted with a primary aromatic amino color-developing agent to form an azomethine linkage.

8. A process according to claim 7 wherein said reaction is carried out in a basic liquid medium in the presence of dimethylformamide and triethylamine.

9. A process according to claim 7 wherein said 4,4-dihalo-5-pyrazolone compound is a 4,4-dibromo-5-pyrazolone compound.

10. A process comprising reacting a 4,4-dibromo-5-pyrazolone color coupler compound with an aromatic compound having the formula $H_2N$-Ar-X wherein Ar is an arylene group containing from 6 to 20 carbon atoms and X is an hydroxy group or an alkylamino group, said process being carried out in a basic liquid medium in the presence of a polar solvent whereby said aromatic compound reacts with said pyrazolone compound to provide a reaction product having an azomethine linkage at the reaction site.

11. A process according to claim 10 wherein the temperature of said reaction is maintained between 10° and 120° C.

12. A process according to claim 10 wherein said reaction product is a compound having the formula:

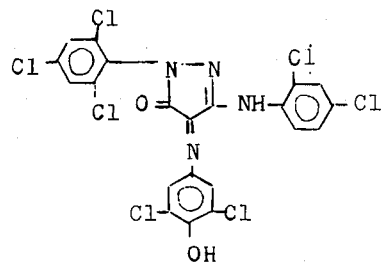

13. A process according to claim 10 wherein said reaction product is a compound having the formula:

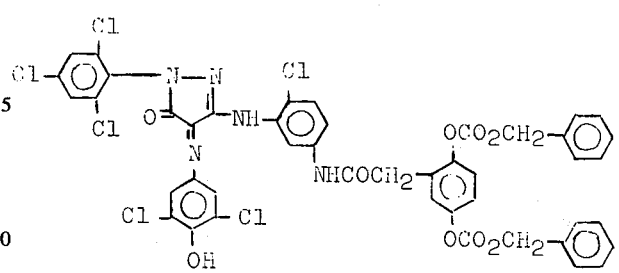

* * * * *